United States Patent [19]

Fooladi

[11] 3,974,093

[45] Aug. 10, 1976

[54] TWO-COMPONENT CATALYST FOR THE PRODUCTION OF SIDE CHAIN HALOGEN SUBSTITUTION PRODUCTS OF AROMATIC COMPOUNDS

[76] Inventor: Mike Mehdi Fooladi, Apt. 4-B, Oakmont Manor Apartments, Vicksburg, Miss. 39180

[22] Filed: Sept. 6, 1974

[21] Appl. No.: 503,981

[52] U.S. Cl............................................ 252/429 R
[51] Int. Cl.² ........................................ B01J 31/02
[58] Field of Search ............ 204/163 R; 260/651 R; 252/429 R, 437

[56] References Cited
UNITED STATES PATENTS
3,707,582   12/1972   Driscoll.......................... 252/429 R Primary Examiner—J. Poer

[57] ABSTRACT

A method is described for the side chain chlorination of alkyl aromatic compounds by chlorination in the presence of a novel catalytic composition comprising phosphorus trichloride and bis (dimethyl thio carbamoyl) di-sulfide. Reaction is with ultra violet light at elevated temperatures.

3 Claims, No Drawings

TWO-COMPONENT CATALYST FOR THE PRODUCTION OF SIDE CHAIN HALOGEN SUBSTITUTION PRODUCTS OF AROMATIC COMPOUNDS

Many attempts have been made in the past to devise a satisfactory method for the production of side chain halogen substituted products of aromatic compounds such as toluene, xylene, mesitylene, and other alkylated aromatic compounds.

The best known of these processes are not completely commercial since they each have a certain disadvantage. For example, prior processes are set forth in U.S. Pat. No. 2,695,873 which describes the use of acid amides; U.S. Pat. No. 1,733,268, which describes the use of phosphorus and sulfur; U.S. Pat. No. 1,345,373 which describes the use of sulfur and acetyl chloride and U.S. Pat. No. 1,384,909, the use of sodium carbonate. In still other methods, diethylamine is employed in U.S. Pat. Nos. 2,034,962; 2,844,635 is concerned with side chain halogenation employing alkylene polyamide, and U.S. Pat. No. 3,363,013 utilizes benzoic peroxide.

Study of the foregoing patents indicates that each of U.S. Pat. Nos. 1,384,909; 1,345,373 and 2,034,962, rejects as an effective catalyst the use of phosphorus trichloride for the chlorination of aromatic side chains.

Taking toluene as representative of aromatic compounds containing alkyl side chains, the chlorinated methyl group of toluene such as benzyl, benzal and benzotrichloride are of commercial interest and are useful intermediates in the chemical industry. Because of their commercial attractiveness, a great deal of research interest continues in the search for better and more economical methods of manufacture.

A most desirable method would eliminate the most troublesome drawbacks now attendant such processes. These disadvantages include difficulty of operation, loss of chlorine, darkening of the product, low yields, poor conversion, polymerization such as formation of tar and gummy materials and ring chlorination, which is the most serious of all.

It is the principal object of this invention to eliminate all of the foregoing deficiencies. It is by means of the novel catalytic composition of this invention that these goals are achieved. In practice, this is accomplished by heating the alkylated ring compound to its boiling point followed by the addition of predetermined quantities of the novel catalytic components such as phosphorus trichloride and bis (dimethyl thio carbamoyl) disulfide. Chlorination is then induced by the introduction of chlorine.

In a preferred embodiment involving the chlorination of the toluene side chain quantities of the foregoing, based on the weight of toluene, may range from 0.5 to 5% phosphorus trichloride, 1.5 to 2.5% preferred and 0.03 – 0.09% of bis (dimethyl thio carbamoyl) disulfide, 0.04 to 0.06% preferred.

With respect to the novel catalyst, the composition by weight, may comprise from 3 to 20 parts of $PCl_3$ and 0.2 to 10 parts of bis (dimethyl thio carbamoyl) disulfide. A preferred composition is generally from about 5 parts of $PCl_3$ to about 1 part of the disulfide. Variations within these ranges are of course permissible and desirable based upon the aromatic compound being chlorinated and the reaction conditions selected.

The invention will be described and illustrated in detail by means of a series of examples which follow, the first group illustrating the prior art and the second group the invention and its advantages. Toluene is the material being chlorinated and all parts are by weight based on the weight of the toluene.

GROUP I

EXAMPLE 1

A glass vessel equipped with condenser, thermometer, and an inlet tube for gaseous chlorine, and an outlet tube for off-gases, was charged with 300 parts of dry toluene. The toluene was brought to its boiling point. Chlorination was then effected for 10 hours in the presence of ultra violet light until all methyl hydrogens were substituted by chlorine. After the theoretical quantity of chlorine was added, a sample was taken and was determined to be 40% benzal and 54% benzotrichloride, and 6% of an unknown material and some tar.

During chlorination the temperature was kept at 110° – 160°C. Chlorination was continued for another 3 hours and a second sample taken for analysis. This sample consisted of 20% of an unknown material, 10% tar, 30% benzal and 40% benzotrichloride. Chlorination was discontinued due to the dark color of the mixture and possible polymerization and ring chlorination.

EXAMPLE 2

Example 1 was repeated twice using 500 parts and 650 parts of toluene. In both instances, the results were very similar to that obtained in Example 1.

EXAMPLE 3

Using apparatus similar to Example 1, 600 parts of dry toluene were reacted with 27.74 parts of $PCl_3$. Chlorination was conducted as in Example 1. At the end of 14 hours a sample was determined to have 66% benzotrichloride, 24% benzal and 10% of an unknown material plus some tar.

EXAMPLE 4

Example 3 was repeated using the same quantity of toluene with varying percentages of $PCl_3$, i.e. 1%, 1.5%, 2.5%, 5% and 5.5 $PCl_3$. In each chlorination, the results showed a greater quantity of benzotrichloride. However, the quantity of tar and unknown substances were also increased.

GROUP II

EXAMPLE 5

Apparatus similar to that used previously was charged with 550 parts of dry toluene, 15 parts of $PCl_3$ and 2.5 parts of bis (dimethyl thio carbamoyl) disulfide. Chorination was as previously described.

Reaction was discontinued after a total of 1460 parts of chlorine were fed to the reactor in 8 hours. The reaction mixture analyzed 97.5% benzotrichloride and 2.5% benzal. The density of the mixture was 1.3890 and crystallization point – 4.5°C.

EXAMPLE 6

1320 parts of dry toluene, 39.6 parts of $PCl_3$, and 2 parts of bis (dimethyl thio carbamoyl) disulfide were charged to a chlorination reactor. Toluene was brought to its boiling point and it was refluxed for 15 minutes. The ultra violet light source was activated and chlorine was introduced into the liquid. When most of the toluene had been converted to benzyl, the reaction temperature was maintained within the range 160°–175°C. During a period of 18 hours, 3,045 parts of chlorine were fed to the reactor with 1459 parts being retained within the reactor and 137 parts appearing in the gas scrubber. Nitrogen was bubbled through the reaction mixture after it cooled. The very light, barely pale yellow crude material was determined to be 98.9% benzotrichloride and 1.1% benzol. The density of the material was 1.3801 at 25°C, and its crystallization point was −4°C.

EXAMPLE 7

A chlorination reactor was charged with 3,000 parts of clean dry toluene. After refluxing for 10 minutes there was added 90 parts of $PCl_3$ and 15 parts of bis (dimethyl thio carbamoyl) disulfide. The solution was refluxed for another 10 minutes. Chlorine was then bubbled into the liquid under ultra violet light. The temperature rose gradually to about 150°C, and then for best chlorination efficiencies was kept at about 155°–185°C, 165–170°C preferred. These temperatures were maintained until no additional absorption of chlorine was apparent, as evidenced by the full conversion of toluene into benzotrichloride.

In a period of 36 hours there was added 7000 parts of chlorine at an average rate of approximately 192 parts per hour. At the end of the chlorination the reactor vessel gained 3,420 parts corresponding to 6,840 parts of reacted chlorine (97.71%) or corresponding to 160 parts of chlorine loss (2.29%). The crude mixture analyzed to 98.5% benzotrichloride and 1.5% benzal.

EXAMPLE 8

A properly equipped chlorination vessel was charged with 1780 parts of dry toluene. Toluene was brought to its boiling point, then refuxed for 15–20 minutes, followed by the addition of 1 part of bis (dimethyl thio carbamoyl) disulfide and 3.56 parts of $PCl_3$. Chlorination was conducted for 13 hours utilizing 4,121 parts of chlorine. The rate of addition was 443 parts 1 hour for the first 7 hours and 364 parts per hour during the second 6 hours. At the end of this period the vessel was cooled and nitrogen bubbled through for one hour until the color was almost colorless. The results of this example are summarized as follows:

| % Benzal | Parts $Cl_2$ Reacted % | Benzal | Parts $Cl_2$ Passed | Density | Temp. C |
|---|---|---|---|---|---|
| 99.8 | 2,001 | 0.2 | 119 | 1.3731 | 165–175 |

EXAMPLE 9

A vessel was charged with 1500 parts of dry toluene, 45 parts of $PCl_3$, .2 parts of bis (dimethyl thio carbamoyl) disulfide. The chlorination was discontinued at the end of 15 hours. The results of this example are summarized as follows:

| Total Parts of $Cl_2$ | Parts $Cl_2$ Reacted | Parts $Cl_2$ Passed | Temp. C. | % Benzo | % Benzal | 20° Crystallization Point°C. |
|---|---|---|---|---|---|---|
| 3,482 | 3,400 | 82 | 160–175 | 99.98 | 0.02 | 1.3722 |

The results shown in the example of Group 1 and 2 clearly show the improvement of this invention resulting from the use of the catalytic composition. The yields of benzotrichloride resulting in the examples of Group II range from 97.5 to 99.98%. The product was almost colorless and substantially free of other chlorinated by-products, unknown substances and tar.

I claim:
1. A chlorination catalyst for chlorination of alkyl aromatic side chains consisting essentially of about 3 to 20 parts by weight of phosphorus trichloride and 0.2 to 10 parts by weight of bis (dimethyl thio carbamoyl) disulfide.
2. The catalyst of claim 1 for the chlorination of toluene.
3. A toluene chlorination catalyst of claim 1 consisting essentially of about 5 parts by weight of $PCl_3$ and about 1 part by weight of the disulfide.

* * * * *